US010006888B2

United States Patent
Humfeld et al.

(10) Patent No.: US 10,006,888 B2
(45) Date of Patent: Jun. 26, 2018

(54) MEMS TRANSDUCERS IN A PHASED ARRAY COUPLED TO A FLEXIBLE SUBSTRATE USING CARBON NANOTUBES FOR CONFORMAL ULTRASOUND SCANNING

(71) Applicant: The Boeing Company, Chicago, IL (US)

(72) Inventors: Keith D. Humfeld, Tukwila, WA (US); Morteza Safai, Newcastle, WA (US)

(73) Assignee: THE BOEING COMPANY, Chicago, IL (US)

( * ) Notice: Subject to any disclaimer, the term of this patent is extended or adjusted under 35 U.S.C. 154(b) by 251 days.

(21) Appl. No.: 15/135,210

(22) Filed: Apr. 21, 2016

(65) Prior Publication Data

US 2017/0307568 A1 Oct. 26, 2017

(51) Int. Cl.
| | | |
|---|---|---|
| *B81C 3/00* | (2006.01) | |
| *G01N 29/04* | (2006.01) | |
| *G01N 29/24* | (2006.01) | |
| *B06B 1/04* | (2006.01) | |
| *C01B 32/16* | (2017.01) | |

(Continued)

(52) U.S. Cl.
CPC ............ *G01N 29/262* (2013.01); *B06B 1/045* (2013.01); *B81C 3/001* (2013.01); *C01B 32/16* (2017.08);
(Continued)

(58) Field of Classification Search
CPC ....... C01B 32/168; C01B 32/16; B81C 3/001; G01N 29/043; G01N 29/2431; G01N 29/262; B06B 1/045
(Continued)

(56) References Cited

U.S. PATENT DOCUMENTS

| | | | | |
|---|---|---|---|---|
| 6,040,611 A | * | 3/2000 | De Los Santos | .. H01H 59/0009 257/414 |
| 6,597,090 B1 | * | 7/2003 | Mancevski | ............ G01Q 70/12 313/309 |

(Continued)

FOREIGN PATENT DOCUMENTS

| | | |
|---|---|---|
| CN | 104090104 | 10/2014 |
| DE | 102010000391 | * 8/2011 |

(Continued)

OTHER PUBLICATIONS

Extended European Search Report dated Aug. 14, 2017 for EP Application No. 17167128.2.
(Continued)

*Primary Examiner* — J M Saint Surin
(74) *Attorney, Agent, or Firm* — Gates & Cooper LLP (57) ABSTRACT

A plurality of micro-electro-mechanical system (MEMS) transducers in a phased array are coupled to a flexible substrate using carbon nanotubes (CNTs) for conformal ultrasound scanning. Each transducer comprises a cantilever, magnetic material deposited on the cantilever, and a solenoid positioned relative to the magnetic material. The carbon nanotubes are grown on the cantilever and mechanically couple the transducer to one side of the flexible substrate. The other side of the flexible substrate is applied to a surface of a part under inspection, and the transducers are electrically connected to a processer to cause movement of the cantilevers when the solenoids are energized by the processor. The movement of the cantilevers results in movement of the carbon nanotubes, which imparts a force to the flexible substrate that results in ultrasound waves, which permeate the part. Returns from the ultrasound waves are interpreted by the processor to generate images of the part.

25 Claims, 9 Drawing Sheets

(51) Int. Cl.
*G01N 29/26* (2006.01)
*C01B 32/168* (2017.01)
*B82Y 30/00* (2011.01)

(52) U.S. Cl.
CPC ......... *C01B 32/168* (2017.08); *G01N 29/043* (2013.01); *G01N 29/2431* (2013.01); *B06B 2201/53* (2013.01); *B81B 2201/0271* (2013.01); *B82Y 30/00* (2013.01); *C01B 2202/08* (2013.01); *G01N 2291/023* (2013.01); *G01N 2291/044* (2013.01); *G01N 2291/0427* (2013.01); *G01N 2291/106* (2013.01); *G01N 2291/2632* (2013.01); *G01N 2291/2638* (2013.01)

(58) Field of Classification Search
USPC .......................................................... 73/625
See application file for complete search history.

(56) References Cited

U.S. PATENT DOCUMENTS

| | | | |
|---|---|---|---|
| 6,925,888 B2 * | 8/2005 | Brossia | G01N 17/00 73/777 |
| 7,545,622 B2 * | 6/2009 | Morris, III | H03H 7/38 361/281 |
| 2008/0305386 A1 * | 12/2008 | Havel | B81B 3/0027 429/50 |
| 2012/0266675 A1 | 10/2012 | Huffman | |
| 2016/0110844 A1 | 4/2016 | Humfeld et al. | |

FOREIGN PATENT DOCUMENTS

| | | | |
|---|---|---|---|
| DE | 102010000392 | * | 8/2011 |
| EP | 1135792 | * | 9/2001 |
| WO | 2015/033190 | | 3/2015 |

OTHER PUBLICATIONS

Nelligan, T., et al., "Knowledge—Intro to Ultrasonic Phased Array", Olympus IMS, http://www.olympus-ims.com/sv/ultrasonics/intro-to-pa/k, pp. 1-8, downloaded Jan. 28, 2016.

Fu, Y.Q., et al., "Process Flow Simulation and Manufacture of Variable RF MEMS Capacitors", The Simulation Standard, Aug. 2005, pp. 5-8.

"Microelectromechanical systems", Wikipedia, http://en.wikipedia.org/wiki/Microelectromechanical_systems, downloaded Feb. 22, 2016.

* cited by examiner

MEMS TRANSDUCERS IN A PHASED ARRAY COUPLED TO A FLEXIBLE SUBSTRATE USING CARBON NANOTUBES FOR CONFORMAL ULTRASOUND SCANNING

CROSS REFERENCE TO RELATED APPLICATION

This application is related to the following co-pending and commonly-assigned application:

U.S. Utility patent application Ser. No. 14/519,839, filed on Oct. 10, 2014, entitled "MULTIPLE PIXEL PITCH SUPER RESOLUTION,";

which application is incorporated by reference herein.

BACKGROUND INFORMATION

1. Field

The invention is related generally to the field of ultrasound transducers (UTs), and more particularly, to micro-electro-mechanical system (MEMS) transducers in a phased array coupled to a flexible substrate using carbon nanotubes (CNTs) for conformal ultrasound scanning.

2. Background

Ultrasound scanning is often used for non-destructive inspection of manufactured parts. For example, an ultrasound scanning apparatus may be comprised of a one-dimensional (1D) or two-dimensional (2D) array of transducers that image a part using ultrasound waves.

Typically, an ultrasound scanning apparatus must be moved back and forth across a surface of a part in order to interrogate different locations on the part. However, such an apparatus works best on flat surfaces, and there can be problems when attempting to scan curved surfaces, especially those containing small radiuses.

For example, if the ultrasound scanning apparatus cannot fit snugly against a small radius, it cannot impart its sonic energy (pressure waves) to the part along the radius, it cannot receive a return, and it cannot measure porosity or detect cracks. This problem arises because the gap between the ultrasound scanning apparatus and the part containing the small radius is filled with a gel that attenuates the signal.

Thus, there is a need for improved apparatus and methods that enable high-resolution, high-contrast, non-destructive, ultrasound scanning for the investigation of shaped parts. The present invention satisfies this need.

SUMMARY

To overcome the limitations in the prior art described above, and to overcome other limitations that will become apparent upon reading and understanding the present specification, the present invention discloses a scanning apparatus for ultrasound inspection of a part, as well as methods of using the apparatus and making the apparatus.

The scanning apparatus is comprised of a flexible substrate, wherein a first side of the flexible substrate is applied to the surface of the part; and one or more MEMS transducers mechanically coupled to a second side of the flexible substrate opposite the first side by one or more carbon nanotubes. Each of the MEMS transducers is comprised of a cantilever, magnetic material deposited on the cantilever, and a solenoid positioned relative to the magnetic material to cause deflection of the cantilever when energized. The carbon nanotubes are grown from the cantilever, so that the deflection of the cantilever results in movement of the carbon nanotubes, which imparts a force to the flexible substrate and creates ultrasound waves that permeate the part.

In one embodiment, the magnetic material comprises magnetically hard materials and a current is applied to the solenoid to create a magnetic field that is aligned with or against a dipole of the magnetic material, the magnetic field bends the cantilever out of plane, and the carbon nanotubes are displaced by the deflection of the cantilever, which imparts the force to the flexible substrate.

In another embodiment, the magnetic material comprises magnetically soft materials and a current is applied to the solenoid to create a magnetic field that polarizes the magnetic material, the magnetic field bends the cantilever out of plane, and the carbon nanotubes are displaced by the deflection of the cantilever, which imparts the force to the flexible substrate.

The method of using the apparatus comprises locating the scanning apparatus on a surface of the part; commanding the scanning apparatus to operate the MEMS transducers, wherein the MEMS transducers are operated to cause movement of the carbon nanotubes, which imparts a force to the flexible substrate that creates ultrasound waves; scanning through the surface of the part using the ultrasound waves; and capturing returns of the ultrasound waves, wherein the captured returns are processed into one or more images of the part.

The commanding step comprises applying a current to the solenoid to create a magnetic field that is applied to the magnetic material on the cantilever, wherein the cantilever responds in a positive or negative direction of the deflection. The commanding step also comprises commanding a change in the deflection of the cantilevers of the MEMS transducers, or commanding a change in phase and frequency of the MEMS transducers, based upon an analysis of the captured returns.

The flexible substrate is not moved laterally along the surface of the part during the scanning step.

In one embodiment, the MEMS transducers form a phased array. In alternate embodiments, the MEMS transducers are operated at an identical frequency and phase, or the MEMS transducers are operated at an identical frequency and different phases, or the MEMS transducers are operated at different frequencies and an identical phase, or the MEMS transducers are operated at different frequencies and different phases. The MEMS transducers are operated at a plurality of frequencies in order to generate a plurality of resolution images of the part from the ultrasound waves.

The method of making the apparatus comprises fabricating one or more MEMS transducers, wherein each of the MEMS transducers is comprised of a cantilever, magnetic material deposited on the cantilever, and a solenoid positioned relative to the magnetic material; growing one or more carbon nanotubes from the cantilever of each of the MEMS transducers; obtaining a flexible substrate, wherein a first side of the flexible substrate is a side of the flexible substrate that is later applied to a surface of a part; and mechanically coupling the MEMS transducers to a second side of the flexible substrate opposite the first side using the carbon nanotubes.

In one embodiment, the method of making further comprises depositing one or more growth catalyst particles for the carbon nanotubes on the cantilever, using masking to prevent deposition in unintended regions, prior to growing the carbon nanotubes from the cantilever. An elastic modulus of the carbon nanotubes is tuned by controlling an areal density of the carbon nanotubes grown from the cantilever.

In one embodiment, the method of making further comprises adding a top layer to each of the MEMS transducers connecting the MEMS transducers.

In another embodiment, the method of making further comprises removing material from between the MEMS transducers to isolate the MEMS transducers.

In still another embodiment, the method of making further comprises adding material between the MEMS transducers to mechanically connect the cantilevers of the MEMS transducers.

DRAWINGS

Referring now to the drawings in which like reference numbers represent corresponding parts throughout.

DETAILED DESCRIPTION

In the following description of the preferred embodiment, reference is made to the accompanying drawings which form a part hereof, and in which is shown by way of illustration a specific embodiment in which the invention may be practiced. It is to be understood that other embodiments may be utilized and structural changes may be made without departing from the scope of the present invention.

Overview

A plurality of MEMS transducers in a phased array are coupled to a flexible substrate by carbon nanotubes for use in conformal ultrasound scanning of a manufactured part. The flexible substrate can be placed on a surface of the part, and every location on the part under the flexible substrate is scanned and imaged precisely by the transducers without moving the flexible substrate or the transducers. The phased array of transducers can operate at a variety of frequencies, so that multiple resolution images of the part can be gathered and combined into super resolution images.

Device Structure and Operation

Figure 1A:
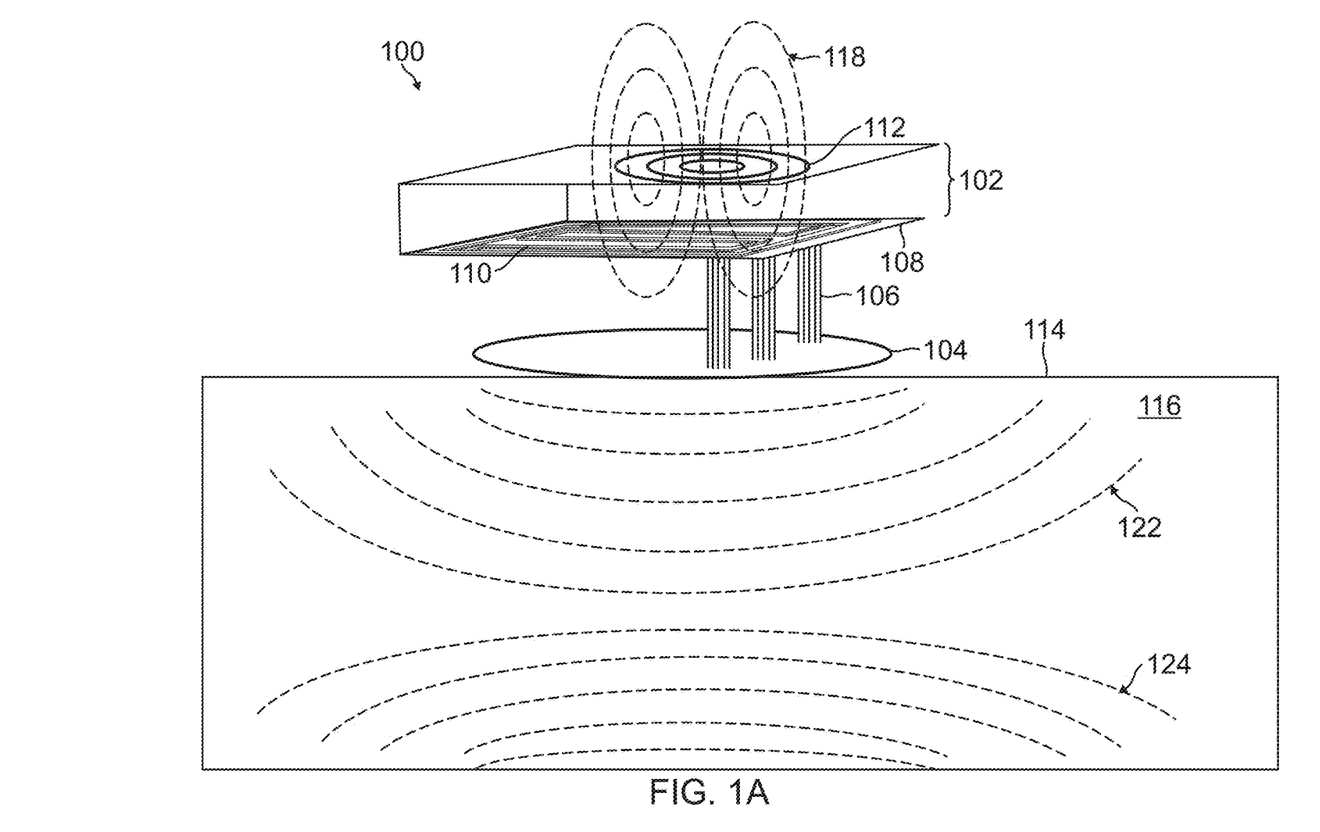
FIGS. 1A, 1B and 1C are schematics of a scanning apparatus according to one embodiment.

FIG. 1A is a schematic of a scanning apparatus 100 according to one embodiment. In this view, one or more ultrasonic transducers 102 are coupled to a flexible substrate 104 by one or more carbon nanotubes 106.

Each transducer 102 includes a cantilever 108 coated on one side (e.g., top) with a magnetic material 110, wherein the cantilever 108 is deflected or moved by operation of a solenoid 112 positioned relative to (e.g., above) the magnetic material 110.

Figure 1B:
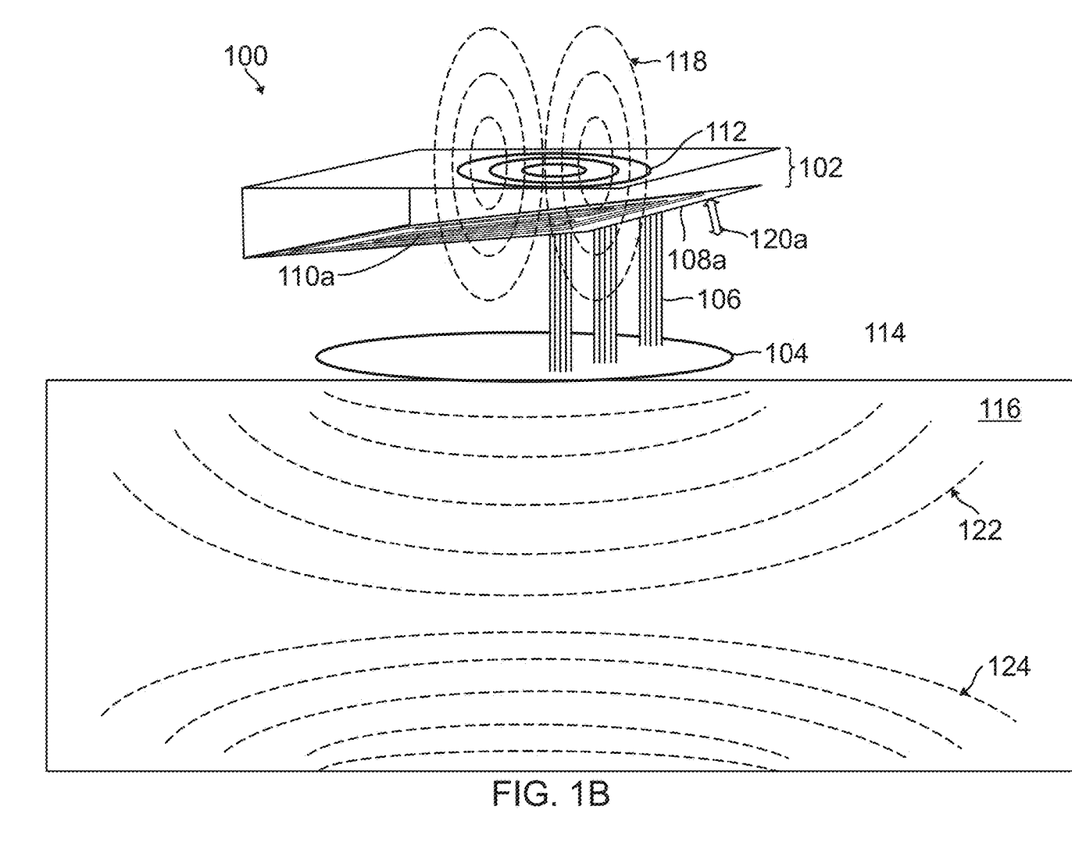
Figure 1C:
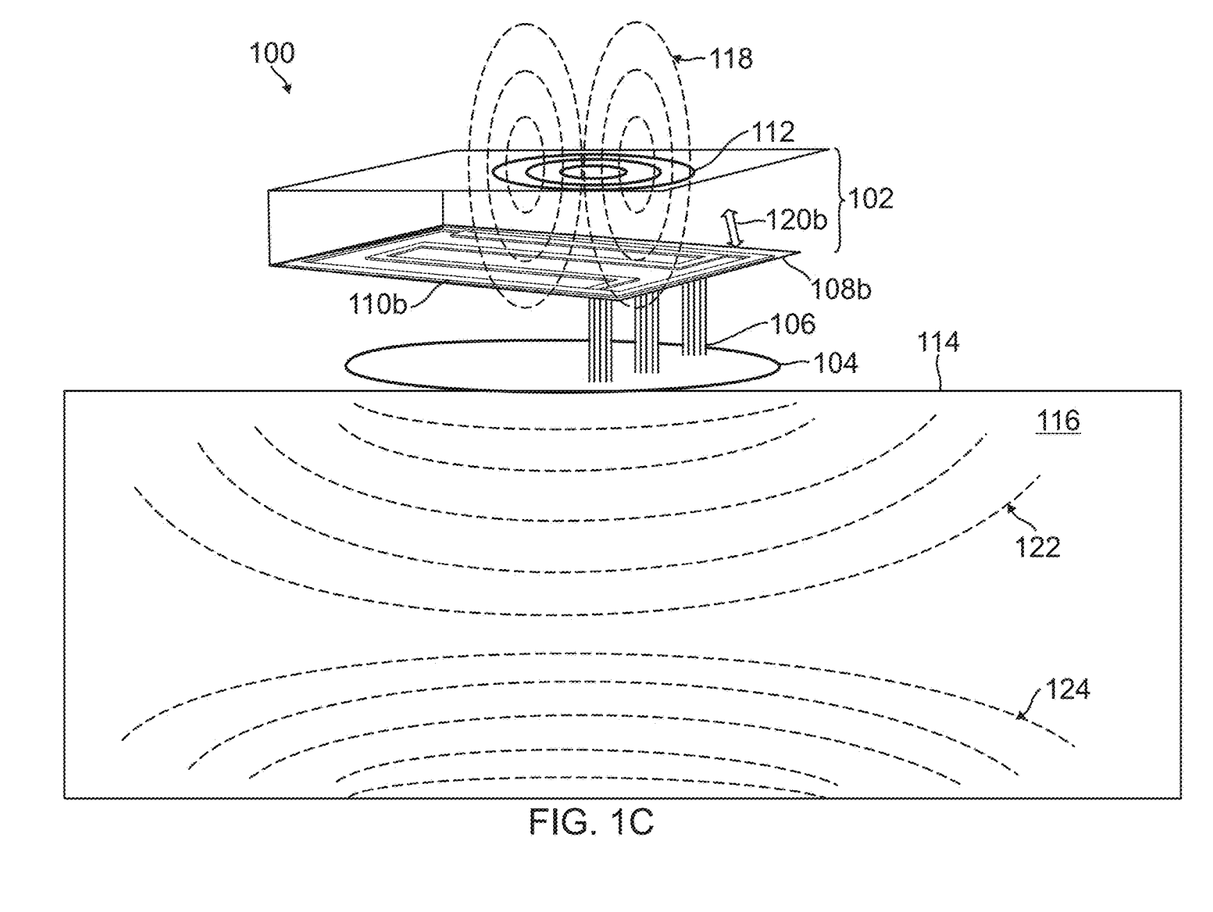

FIG. 1A shows the transducer 102 with the cantilever 108 and magnetic material 110 at rest, while FIG. 1B shows the transducer 102 with the cantilever 108a and magnetic material 110a deflected upward and FIG. 1C shows the transducer 102 with the cantilever 108b and magnetic material 110b deflected downward.

The carbon nanotubes 106 are grown on another side of (e.g., underneath) the cantilever 108 opposite the side of the cantilever 108 coated with the magnetic material 110. Following growth, an opposite end of the carbon nanotubes 106 is coupled to the flexible substrate 104.

The flexible substrate 104 is a Teflon membrane, but could be a different material. When the carbon nanotubes 106 are pressed against the flexible substrate 104, the carbon nanotubes 106 become tightly coupled to the flexible substrate 104.

The operation of the scanning apparatus 100 is described as follows. A first side of the flexible substrate 104 is applied to or laid on a surface 114, which may be a flat or curved surface 114, of a part 116 under inspection. Each transducer 102 is coupled to a second side of the flexible substrate 104 opposite the first side by the carbon nanotubes 106. In one embodiment, the flexible substrate 104 is not moved laterally along the surface 114 of the part 116 during the operation.

A processor (not shown) applies a current to the solenoid 112, which creates a magnetic field, labeled as 118, that is applied to the magnetic material 110 on the cantilever 108. This causes a magnetic force that bends the cantilever 108 out of plane, either up or down, wherein FIG. 1A shows the cantilever 108 and magnetic material 110 in-plane (e.g., at rest), FIG. 1B shows the cantilever 108a and magnetic material 110a out-of-plane (e.g., bent upward along an arc of movement 120a), and FIG. 1C shows the cantilever 108b and magnetic material 110b out-of-plane (e.g., bent downward along an arc of movement 120b).

The carbon nanotubes 106 attached to the underside of the cantilever 108 are moved up and/or down (e.g., stretch and/or compress) by the motion of the cantilever 108 and magnetic material 110, which expresses a force (pull and/or push) on the flexible substrate 104 coupled to the other end of the carbon nanotubes 106, creating ultrasound waves, labeled as 122, which are pressure waves, that spread out from the location of the transducer 102 and permeate the part 116.

Similarly, a return or reflection 124 is received from the ultrasonic waves 122, which expresses a force (pull and/or push) on the flexible substrate 104, causing an up and/or down motion of the carbon nanotubes 106, resulting in the up and/or down motion of the cantilever 108. The corresponding movement of the magnetic material 110 in the magnetic field 118 causes a current in the solenoid 112, which is then transmitted the processor for processing. Specifically, the processor can generate images from the signals received from the transducers 102, as described in more detail below.

Note that, in alternate embodiments, the magnetic material 110 is comprised of hard or soft magnetic material. When the magnetic material 110 is comprised of hard magnetic material, it has a dipole and the magnetic field created by the solenoid 112 that is either aligned with or against the dipole of the magnetic material 110 bends the cantilever 108 up and/or down. When the magnetic material 110 is comprised of soft magnetic material, it is a collection of magnetically soft microparticles, such as iron, which are magnetically polarized by the magnetic field created by the solenoid 112 and experience a force attracting them to the solenoid 112, such that a current applied to the solenoid 112 bends the cantilever 108 toward the solenoid 112, and the cantilever 108 relaxes when the current to the solenoid 112 is removed.

Figure 1D:
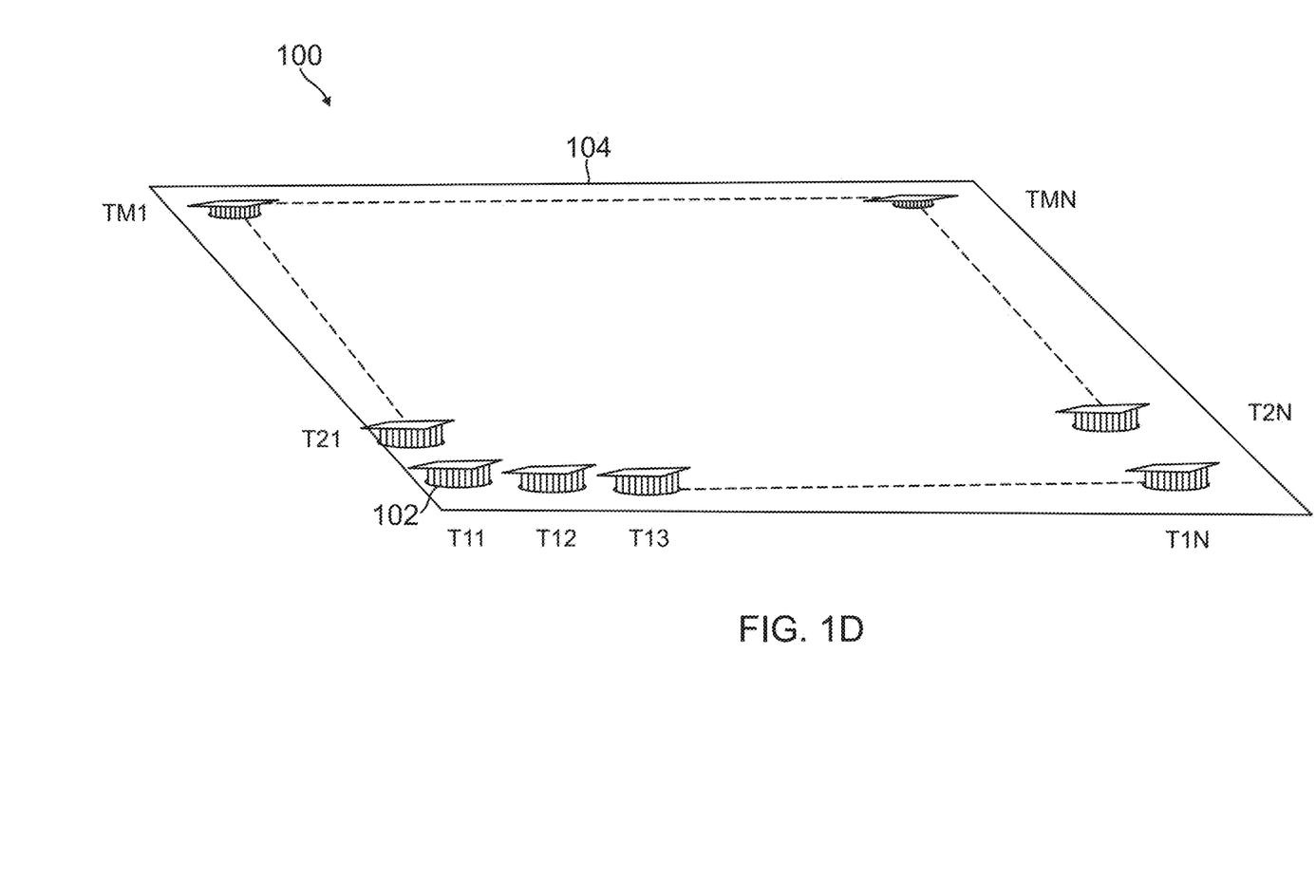
FIGS. 1D, 1E and 1F illustrate how the scanning apparatus is comprised of a plurality of transducers arranged in an array, and the array is operated as a phased array by controlling the transducers individually and collectively.
Figure 1E:
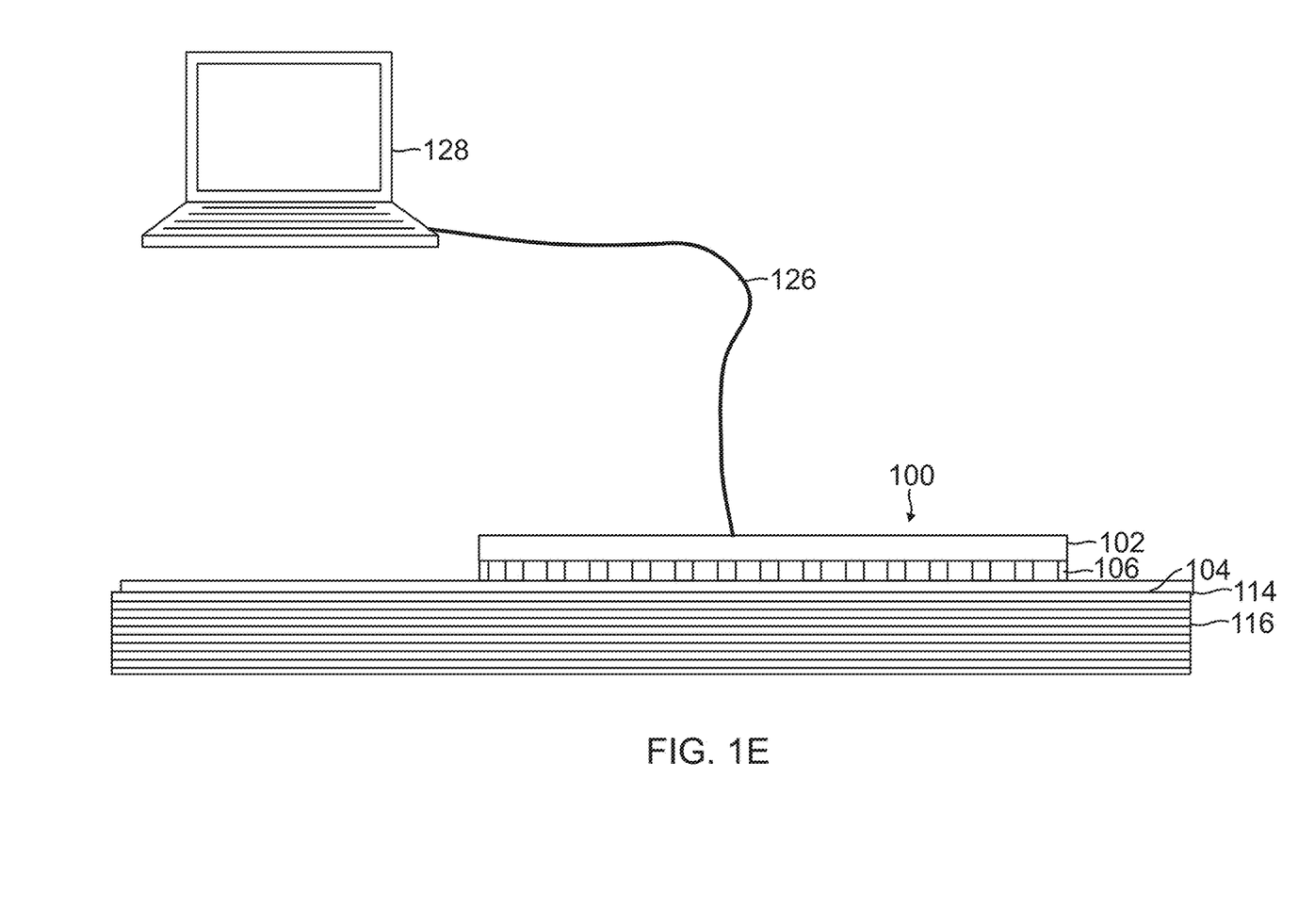
Figure 1F:
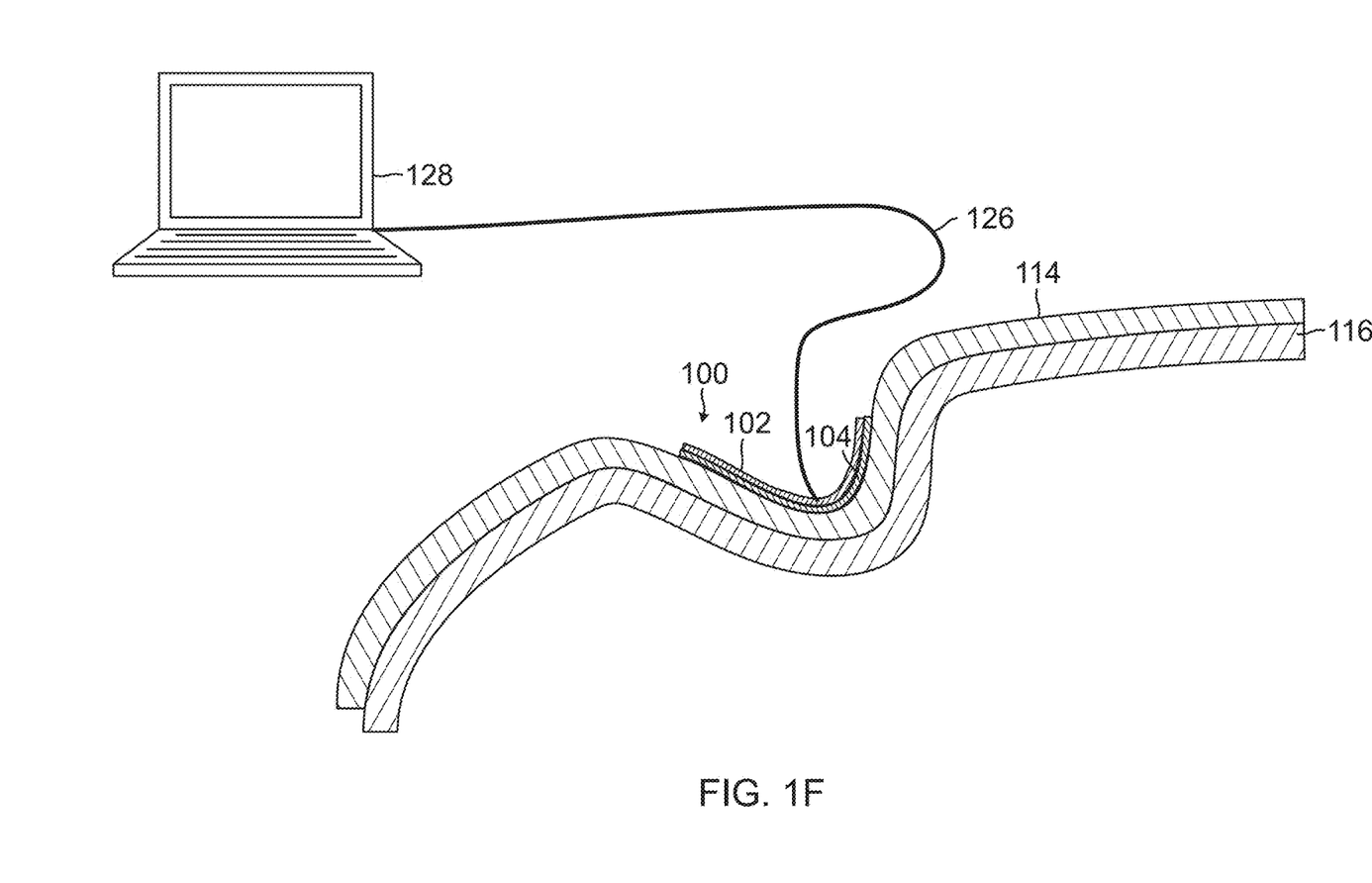

FIGS. 1D, 1E and 1F illustrate how the scanning apparatus 100 is comprised of a plurality of transducers 102 arranged in a 2D array, and the 2D array is operated as a phased array by controlling the transducers 102 individually and/or collectively.

In the example of FIG. 1D, the 2D array of transducers 102 is arranged as a matrix on the flexible substrate 104. The transducers 102 in the matrix are labeled as T11, T12, T13, . . . , T1N in a first row; T21, . . . , T2N in a second row; and TM1, . . . , TMN in an Mth row. Consequently, a fully populated matrix would comprise M×N transducers 102, although only a subset of the M×N transducers 102 is shown in FIG. 1D.

In the example of FIG. 1E, a first side of the flexible substrate 104 is applied to or laid on the surface 114, which is a flat surface 114, of the part 116 under inspection. The transducers 102 are coupled to a second side of the flexible substrate 104 opposite the first side by the carbon nanotubes 106. In this example, the transducers 102 are electrically connected via a cable 126 to a processor 128, which commands the scanning apparatus 100 by individually and collectively controlling the transducers 102. In an alternative embodiment, the transducers 102 are connected wirelessly to the processor 128.

In the example of FIG. 1F, a first side of the flexible substrate 104 is applied to or laid on the surface 114, which is a curved surface 114, of the part 116 under inspection. The transducers 102 coupled to a second side of the flexible substrate 104 opposite the first side are electrically connected via a cable 126 to a processor 128, which commands the scanning apparatus 100 by individually and collectively controlling the transducers 102.

In one embodiment, the processor 128 addresses all of the transducers 102 at the same time. In another embodiment, the processor 128 addresses individual transducers 102 or subsets of the transducers 102, singly or in some sequence.

In one embodiment, the processor 128 operates the transducers 102 at the same frequency and/or the same or different phases. In another embodiment, the processor 128 operates the transducers 102 at different frequencies and/or the same or different phases.

In all embodiments, the processor 128 applies a positive or negative voltage to the solenoid 112 for each transducer 102, and each cantilever 108 responds in either a positive or negative direction of deflection. The frequency-dependent impedance of the solenoid 112 smooths these signals into a controlled (phase and amplitude) deflection of the cantilever 108, which results in the movement of the carbon nanotubes 110 and imparts a force onto the flexible substrate 104.

In one embodiment, the frequency at which each transducer 102 is operated by the processor 128 is the same, but the phases are different, wherein the processor 128 communicates a "phase image" to the array of transducers 102, in which each "pixel" of the phase image represents a phase to be imposed on each transducer 102 in the array. The result is that the plurality of transducers 102 operates as a phased array.

There are a number of benefits to the use of a phased array of transducers 102. For example, the processor 128 can modulate the phase of each transducer 102 relative to its neighboring transducers 102, which enables the processor 128 to choose a specific location for constructive interference of the ultrasound waves 122 imparted to the part 116 being investigated. This greatly increases the net amplitude at that location, decreasing power needs. Further, the location at which constructive interference occurs can be changed by modifying the relative phases of the transducers 102, so that the part 116 being investigated can be scanned from one side of the array to the other, without moving the array of transducers 102.

Moreover, the phased array of transducers 102 not need to be limited to a particular frequency. Each cantilever 108 has a characteristic frequency, but if the resonance of the cantilevers 108 is not necessary to obtain an amplitude signal, then the transducers 102 can be driven at any appropriate frequency or even at multiple frequencies, which in ultrasound testing generally occurs in the range of 0.5-5.0 MHz.

The attenuation of the ultrasound waves 122 in the part 116, and the signal-to-noise ratio (SNR) for the returns 124 of the ultrasound waves 122 reflecting from a pore, crack or other feature of the part 116, are both dependent on the frequency. After detection by the array of transducers 102 and processing by the processor 128, this results in a frequency-dependent spatial resolution.

For example, the processor 128 can form a super resolution image using the system described in U.S. Utility patent application Ser. No. 14/519,839, filed on Oct. 10, 2014, entitled "MULTIPLE PIXEL PITCH SUPER RESOLUTION,", which is cross-referenced above and incorporated by reference herein.

Specifically, if a series of returns 124 are collected at different resolutions, and the features causing the returns 124 do not change (a good assumption for most parts 116 being investigated with ultrasound waves 122), the multiple returns 124 can be combined by the processor 128 to form a super resolution image. This can be accomplished because the part 116 is scanned spatially (at a given frequency) without moving the transducers 102, which means that the part 116 can be scanned repeatedly at different frequencies with no spatial uncertainty.

Device Operation

Figure 2:
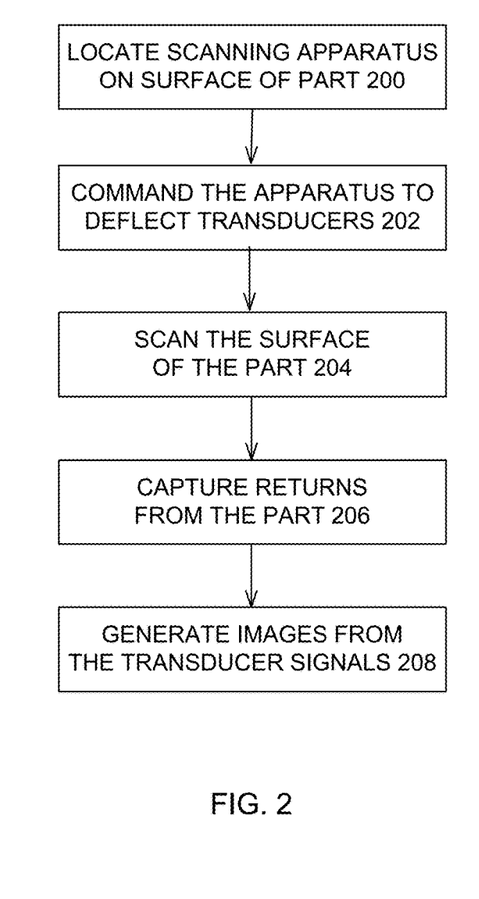
FIG. 2 is a flowchart that illustrates the operation of the scanning apparatus according to one embodiment.

FIG. 2 is a flowchart that illustrates the operation of the scanning apparatus according to one embodiment.

Block 200 represents the step of locating the scanning apparatus on a surface of a part to be scanned. Specifically, a first side of the flexible substrate is applied to or laid on the surface of the part to be scanned, which may be a flat or curved surface. In one embodiment, the flexible substrate is not moved laterally along the surface of the part during the operation.

As noted above, the transducers are mechanically coupled to a second side of the flexible substrate opposite the first side by the carbon nanotubes. These transducers are electrically connected to a processor, which individually and collectively controls the transducers.

Block 202 represents the step of commanding the scanning apparatus to operate the transducers, wherein the transducers are operated to energize the solenoids to deflect the cantilevers relative to the surface of the part being scanned and inspected. In this step, the processor addresses the transducers, and applies a positive or negative voltage to the solenoid for each transducer. The current applied to the solenoid creates a magnetic field that is applied to the magnetic material on the cantilever, and each cantilever responds in either a positive or negative direction of deflection, based on the positive or negative voltage, respectively Block 204 represents the step of scanning the part using the ultrasound waves created by the movement of the carbon nanotubes, which imparts a force to the flexible substrate. In this step, the carbon nanotubes attached to the underside of the cantilever are moved up and/or down by the motion of the cantilever, imparting the force to the flexible substrate and thereby creating ultrasound waves that permeate the part.

Block 206 represents the step of capturing and collecting returns or reflections of the ultrasound waves from the surface of the part, wherein the captured returns generate signals in the transducers that are processed into one or more images of the part. In this step, the returns express a force on the flexible substrate, causing an up and/or down motion of the carbon nanotubes, resulting in the up and/or down motion of the cantilever. The corresponding movement of the magnetic material in the magnetic field causes a current in the solenoid, which is then transmitted to the processor as a positive or negative voltage for processing.

Block 208 represents the step of generating images in the processor from the signals received from the transducers. In this step, the processor also commands a change in the deflection based upon analysis of the captured returns, including commanding a change in the phase and frequency based upon analysis of the captured returns.

Device Fabrication

Figure 3:
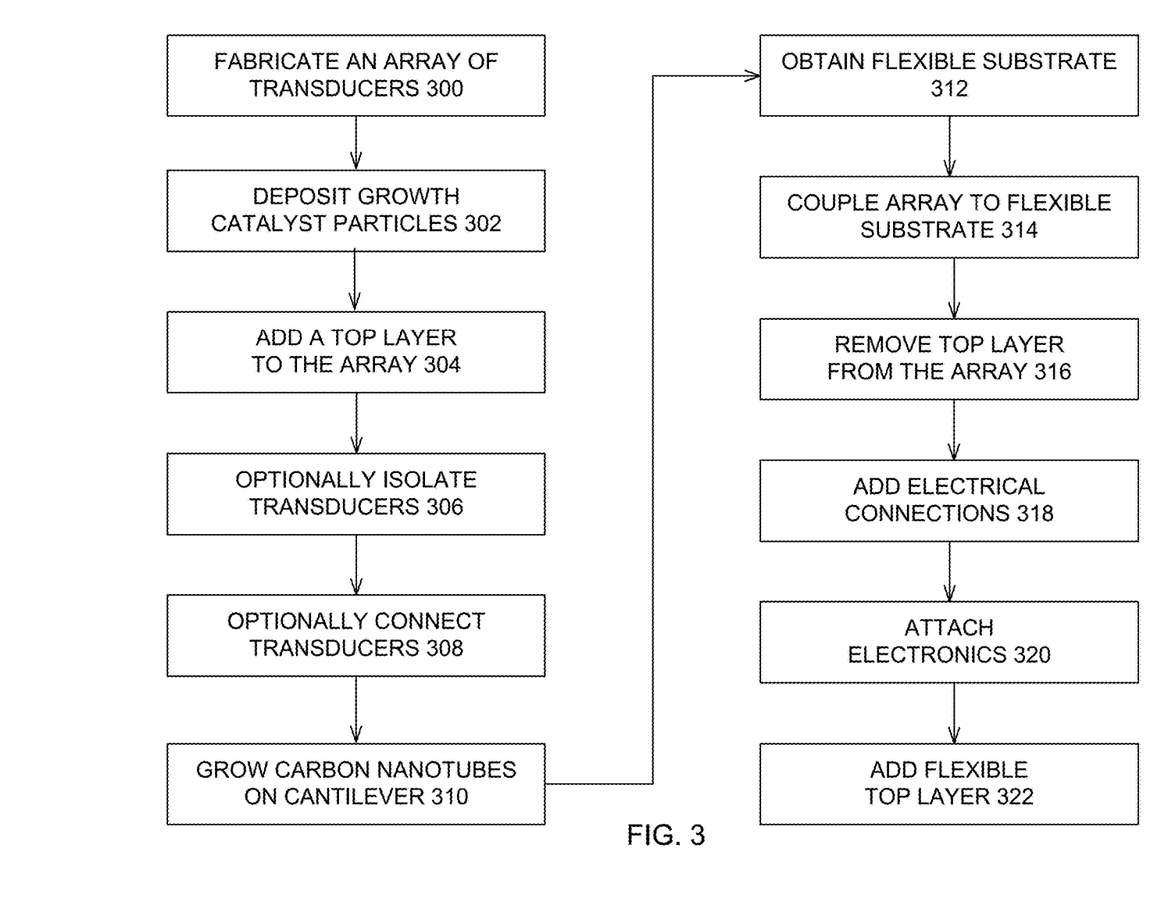
FIG. 3 is a flowchart that illustrates the fabrication of the scanning apparatus according to one embodiment.

FIG. 3 is a flowchart that illustrates the fabrication of the scanning apparatus according to one embodiment.

Block 300 represents the step of fabricating an array of ultrasonic transducers on a silicon wafer, including the fabrication of a cantilever, magnetic material and solenoid in each transducer. This is described in more detail in FIG. 4 below.

Block 302 represents the step of depositing carbon nanotube growth catalyst particles on the cantilevers, using masking to prevent deposition in unintended regions of the cantilevers. This is also described in more detail in FIG. 4 below.

Block 304 represents the step of adding a rigid, dissolvable or otherwise removable top layer (such as a temperature-limited adhesive top layer) to the array of transducers as a support structure.

Block 306 represents the step of optionally removing silicon from between the transducers to mechanically isolate each of the transducers.

Block 308 represents the step of optionally adding silicone or other flexible material between the transducers to mechanically connect each of the transducers.

Block 310 represents the step of using carbon vapor deposition to grow carbon nanotubes from the growth catalyst particles on the cantilever of each transducer.

Block 312 represents the step of obtaining a flexible substrate.

Block 314 represents the step of mechanically coupling the array of transducers to the flexible substrate (e.g., while it is flat), wherein the carbon nanotubes on the cantilevers contact the flexible substrate in a direction normal to the surface of the flexible substrate. In this step, the carbon nanotubes are conditioned by compressing and relaxing them against the surface of the flexible substrate for some number of cycles, which typically comprises thousands of cycles.

Block 316 represents the step of removing the top layer between the transducers, so that the structure of the scanning apparatus is comprised only of the flexible substrate, carbon nanotubes and transducers.

Block 318 represents the step of adding or attaching electrical connections to each of the transducers.

Block 320 represents the step of adding or attaching any necessary electronics to each of the transducers.

Block 322 represents the step of optionally adding a flexible top layer between the transducers as a support structure, so that the structure of the scanning apparatus is comprised of the substrate, carbon nanotubes, transducers and flexible top layer.

FIG. 3 is only one example of a fabrication process that would result in the scanning apparatus. However, different processes with different steps could also be used to fabricate the scanning apparatus described herein.

The carbon nanotubes' fabrication is generally compatible with the MEMS fabrication of the substrate, cantilever, spacer, solenoid and packaging components, which is described below in FIG. 4. The MEMS fabrication of these components are capable of withstanding some temperatures at which carbon nanotubes can be grown via chemical vapor deposition (CVD). Further, the carbon nanotubes' growth catalyst particles can be deposited on the underside of the cantilever during MEMS fabrication.

While any material could be used for this purpose, the carbon nanotubes have a number of advantages over other materials. For example, the carbon nanotubes each have one end that terminates against a surface of the flexible substrate, wherein some length of each carbon nanotube bends to lie on the surface. This creates a strong adhesive interaction between each contacting carbon nanotube and the surface. Thus, each of the vertically-aligned carbon nanotubes adheres to the flexible substrate without any adhesive, and with no special alignment or registration of position with features on the substrate. Specifically, there is no need for perfect alignment of the flexible substrate with the carbon nanotubes extending from the cantilevers, which would likely be necessary if another material, such as rubber posts, were used to connect the cantilevers with the flexible substrate.

Another advantage is that the elastic modulus of the carbon nanotubes can be tuned by controlling the areal density of the carbon nanotubes extending from each cantilever. This allows modulus matching of the carbon nanotubes to the underlying flexible substrate, which will aid in generating physical resonance in the mechanical motion, which is helpful for reducing the power needs on the driving solenoids.

Another advantage is that different sections of the carbon nanotubes can be flexed more or less at the same time, so the change in angle of the cantilever during deflection does not cause torque on the carbon nanotubes, which could cause mechanical failure of the carbon nanotubes.

These and other benefits result from growing nanotubes on the underside of the cantilever to mechanically couple the cantilever to the flexible surface for phased array ultrasonic scanning, in order to transmit the vibration of the cantilever into the part being scanned. Moreover, because each MEMS transducer is inherently small and need not be strongly mechanically coupled to its neighboring transducers, an array of transducers can be constructed on a flexible substrate to make a phased array for conformal ultrasound scanning.

Transducer Fabrication

Figure 4:
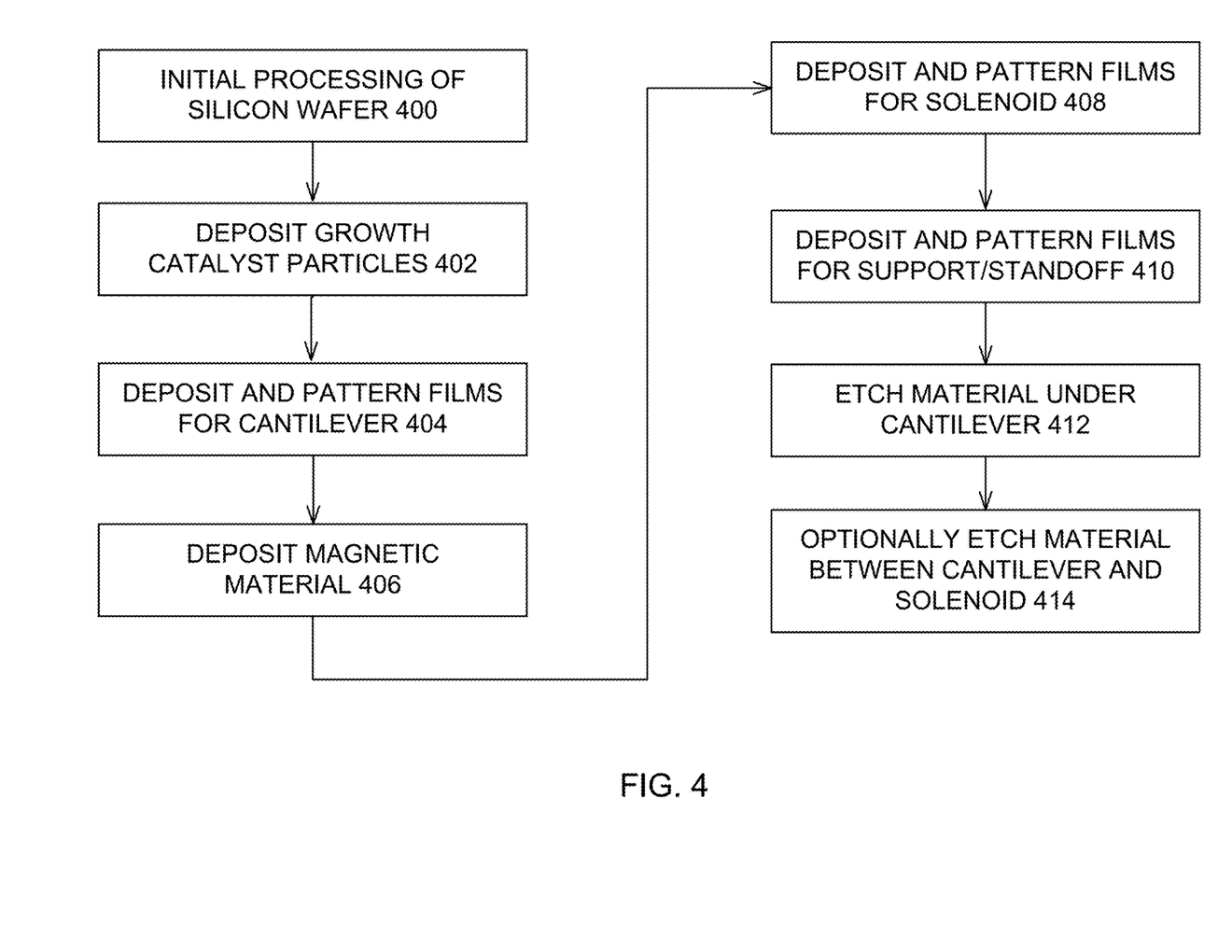
FIG. 4 is a flowchart that illustrates the fabrication of the transducers according to one embodiment.

FIG. 4 is a flowchart that illustrates the fabrication of the transducers according to one embodiment.

Block 400 represents the step of initial processing of a silicon wafer. For example, the initial processing includes the deposition and patterning of Cr electrodes, $HfO_2$ film deposition and patterning by sputtering, and $SiO_2$ film deposition and patterning by plasma-enhanced chemical vapor deposition (PECVD).

Block 402 represents the step of depositing carbon nanotube growth catalyst particles. The carbon nanotube growth catalyst particles, such as small domains of Fe, Ti, or Co, are deposited on regions corresponding to the places on the cantilever where carbon nanotube growth is desired.

Block 404 represents the step of depositing and patterning films for the cantilever. The cantilever includes PECVD a-Si:H film deposition and patterning.

Block 406 represents the step of depositing films for the magnetic material. The magnetic material includes deposition of a layer of magnetic particles, either hard magnets such as FeCo or $SmCo_5$, or soft magnets such as Fe, on top of the cantilever.

If it is desired to fabricate the solenoid over the cantilever during the same fabrication process, the following steps are then performed.

Block 408 represents the step of depositing and patterning films for the solenoid. The solenoid includes PECVD $SiO_2$ film deposition and patterning with the same pattern/mask as used in Block 304, and sputtered Cu film deposition and patterning, which forms the solenoid and its lead wires.

Block 410 represents the step of depositing and patterning films for the support and standoff for the solenoid, wherein the support is the layer above the solenoid and the standoff connects the support to the cantilever. The support and standoff for the solenoid includes PECVD a-Si:H film deposition to build the standoff for the solenoid and the support for the solenoid. In this example, the solenoid support covers the entire surface and need not be patterned.

Note that Blocks 408 and 410 may be in reversed order, resulting in a reversed order of films.

Block 412 represents the step of etching the material under the cantilever.

Block 414 represents the step of optionally etching the material between the cantilever and the solenoid, as well as optionally etching some or all of the material between transducers. In this step, the etching of some of the material between transducers results in an array of transducers on a mesh created from the silicon wafer.

FIG. 4 is only one example of a fabrication process that would result in the MEMS transducers including cantilevers ready for carbon nanotube growth. However, different processes with different steps could be used to fabricate the MEMS transducers described herein.

Alternatives

The description of the different embodiments set forth above has been presented for purposes of illustration and description, and is not intended to be exhaustive or limited to the embodiments in the form disclosed. Many modifications and variations will be apparent to those of ordinary skill in the art.

Specifically, the ultrasonic transducers, carbon nanotubes and flexible substrate may comprise structures and materials different from those disclosed herein. Moreover, different processes and steps may be used to fabricate and operate the scanning apparatus and transducers. Finally, the array of transducers may be arranged in different arrays from those disclosed herein.

It is intended that the scope of the invention be limited not by this detailed description, but rather by the claims appended hereto.

What is claimed is:

1. An apparatus for inspecting a part, comprising:
   (a) a flexible substrate, wherein a first side of the flexible substrate is applied to a surface of a part; and
   (b) one or more micro-electro-mechanical system (MEMS) transducers mechanically coupled to a second side of the flexible substrate opposite the first side by one or more carbon nanotubes (CNTs);
   (c) wherein each of the MEMS transducers is comprised of a cantilever, magnetic material deposited on the cantilever, and a solenoid positioned relative to the magnetic material to cause deflection of the cantilever when energized;
   (d) wherein the carbon nanotubes are grown from the cantilever, so that the deflection of the cantilever results in movement of the carbon nanotubes, which imparts a force to the flexible substrate to create ultrasound waves that permeate the part; and
   (e) wherein one or more of the MEMS transducers are operated to generate the ultrasound waves and to receive returns from the ultrasound waves, and the returns are interpreted for inspecting the part.

2. The apparatus of claim 1, wherein the magnetic material comprises magnetically hard materials and a current is applied to the solenoid to create a magnetic field that is aligned with or against a dipole of the magnetic material, the magnetic field bends the cantilever out of plane, and the carbon nanotubes are displaced by the deflection of the cantilever, which imparts the force to the flexible substrate.

3. The apparatus of claim 1, wherein the magnetic material comprises magnetically soft materials and a current is applied to the solenoid to create a magnetic field that polarizes the magnetic material, the magnetic field bends the cantilever out of plane, and the carbon nanotubes are displaced by the defection of the cantilever, which imparts the force to the flexible substrate.

4. A method for inspecting a part, comprising:
   (a) locating a scanning apparatus on a surface of a part, wherein the scanning apparatus is comprised of a flexible substrate applied to the surface and one or more micro-electro-mechanical system (MEMS) transducers mechanically coupled to the flexible substrate by one or more carbon nanotubes (CNTs);
   (b) commanding the scanning apparatus to operate the MEMS transducers, wherein the MEMS transducers are operated to cause movement of the carbon nanotubes, which imparts a force to the flexible substrate that creates ultrasound waves;
   (c) scanning through the surface of the part using the ultrasound waves; and
   (d) capturing returns of the ultrasound waves from the surface of the part.

5. The method of claim 4, wherein each of the MEMS transducers is comprised of a cantilever, magnetic material deposited on the cantilever, and a solenoid positioned relative to the magnetic material to cause deflection of the cantilever when energized, and the carbon nanotubes are grown from the cantilever, so that the deflection of the cantilever results in the movement of the carbon nanotubes.

6. The method of claim 5, wherein the commanding step comprises commanding a positive or a negative direction of deflection of the cantilever.

7. The method of claim 6, wherein the commanding step comprises applying a current to the solenoid to create a magnetic field that is applied to the magnetic material on the cantilever, wherein the cantilever responds in the positive or negative direction of the deflection.

8. The method of claim 6, wherein the commanding step comprises commanding a change in the deflection of the cantilevers of the MEMS transducers based upon an analysis of the captured returns.

9. The method of claim 4, wherein the commanding step comprises commanding a change in phase and frequency of the MEMS transducers based upon an analysis of the captured returns.

10. The method of claim 4, wherein the locating step comprises conforming the flexible substrate to the surface.

11. The method of claim 4, wherein the flexible substrate is not moved laterally along the surface of the part during the scanning step.

12. The method of claim 4, wherein the MEMS transducers form a phased array.

13. The method of claim 4, further comprising operating the MEMS transducers at an identical frequency and phase.

14. The method of claim 4, further comprising operating the MEMS transducers at an identical frequency and different phases.

15. The method of claim 4, further comprising operating the MEMS transducers at different frequencies and an identical phase.

16. The method of claim 4, further comprising operating the MEMS transducers at different frequencies and different phases.

17. The method of claim 4, further comprising operating the MEMS transducers at a plurality of frequencies in order to generate a plurality of resolution images of the part from the ultrasound waves.

18. The method of claim 4, further comprising processing the captured returns into one or more images of the part.

19. A method for making a scanning apparatus for inspecting a part, comprising:
 (a) fabricating one or more micro-electro-mechanical system (MEMS) transducers, wherein each of the MEMS transducers is comprised of a cantilever, magnetic material deposited on the cantilever, and a solenoid positioned relative to the magnetic material;
 (b) growing one or more carbon nanotubes (CNTs) from the cantilever of each of the MEMS transducers;
 (c) obtaining a flexible substrate, wherein a first side of the flexible substrate is a side of the flexible substrate that is later applied to a surface of a part; and
 (d) mechanically coupling the MEMS transducers to a second side of the flexible substrate opposite the first side using the carbon nanotubes.

20. The method of claim 19, wherein, when the first side of the flexible substrate is applied to the surface of the part, the solenoids of the MEMS transducers are energized to cause deflection of the cantilevers of the MEMS transducers, the deflection of the cantilevers of the MEMS transducers results in movement of the carbon nanotubes, which imparts a force to the flexible substrate to create ultrasound waves that permeate the part, and returns from the ultrasound waves are interpreted for inspecting the part.

21. The method of claim 19, wherein an elastic modulus of the carbon nanotubes is tuned by controlling an areal density of the carbon nanotubes grown from the cantilever.

22. The method of claim 19, further comprising depositing one or more growth catalyst particles for the carbon nanotubes on the cantilever, using masking to prevent deposition in unintended regions, prior to growing the carbon nanotubes from the cantilever.

23. The method of claim 19, further comprising adding a top layer to each of the MEMS transducers connecting the MEMS transducers.

24. The method of claim 19, further comprising removing material from between the MEMS transducers to isolate the MEMS transducers.

25. The method of claim 19, further comprising adding material between the MEMS transducers to mechanically connect the cantilevers of the MEMS transducers.

* * * * *